United States Patent
Krettek et al.

[19]

[11] Patent Number: 6,039,742
[45] Date of Patent: Mar. 21, 2000

[54] ALIGNMENT DEVICE FOR LOCKING THE BASE PART OF INTRAMEDULLARY NAILS

[75] Inventors: Christian Krettek, Hannover; Bernd Könemann, Celle, both of Germany; Alexandre Perrier, Basel; Peter Senn, Waldenburg, both of Switzerland

[73] Assignee: Synthes (U.S.A.), Paoli, Pa.

[21] Appl. No.: 09/185,130

[22] Filed: Nov. 3, 1998

Related U.S. Application Data

[63] Continuation of application No. PCT/CH97/00172, May 2, 1997.

[51] Int. Cl.[7] ............................. A61B 17/58; A61B 17/00
[52] U.S. Cl. .................................................. 606/96; 606/9
[58] Field of Search ................................. 606/98, 97, 96, 606/86, 62, 63, 64

[56] References Cited

U.S. PATENT DOCUMENTS

| | | |
|---|---|---|
| 3,616,837 | 11/1971 | Mollard . |
| 4,541,424 | 9/1985 | Grosse et al. . |
| 5,620,449 | 4/1997 | Faccioli et al. . |
| 5,766,179 | 6/1998 | Faccioli et al. ............................ 606/98 |

FOREIGN PATENT DOCUMENTS

| | | |
|---|---|---|
| WO 9201422 | 2/1992 | WIPO . |
| WO 9603085 | 2/1996 | WIPO . |

*Primary Examiner*—Gary Jackson
*Assistant Examiner*—Vy Q. Bui
*Attorney, Agent, or Firm*—Pennie & Edmonds LLP

[57] ABSTRACT

The alignment device serves for the positioning and insertion of osteosynthetic fasteners, in particular locking screws or bolts, in the base part of an intramedullary nail implanted in a bone, with an alignment bracket detachably connected to the top end of the intramedullary nail, and with a longitudinal alignment bar attached to the bracket by means of a coupling unit, the bar having a first section and a second section. In the first section, the alignment bar is detachably and movably connected to a coupling unit. By way of the coupling unit, the alignment bar is also detachably and pivotably connected to the alignment bracket. The second section of the alignment bar is provided with at least one guide hole serving to permit the positioning of a bore for locking the base of the intramedullary nail in a bone. The second section of the alignment bar also supports a lockable first spacing-sensor assembly with a spacing sensor whose contact surface making contact with the surface of the base of the intramedullary nail permits a shift perpendicular to the intramedullary nail without losing contact with the nail. In addition, a second spacing-sensor assembly is provided, consisting of an alignment bridge supporting on one side a contactor which is oriented toward a locking hole in the base of the nail and is provided on the other side with guide holes which serve to permit the positioning and insertion of osteosynthetic fasteners in the base part of the nail implanted in a bone. In this manner, the intramedullary nail can be distally locked in two planes in a radially fixed, rotation-resisting position, which constitutes a clinical advantage over conventional systems.

19 Claims, 4 Drawing Sheets

ALIGNMENT DEVICE FOR LOCKING THE BASE PART OF INTRAMEDULLARY NAILS

This application is a Continuation of PCT/CH97/00172 filed May 2, 1997.

TECHNICAL FIELD

This invention relates to an alignment system serving to position and insert osteosynthetic fasteners, in particular locking screws or bolts, in the base of an intramedullary nail.

BACKGROUND ART

Successful positioning of locking screws in the base of a retaining intamedullary nail is a difficult and time-consuming undertaking. The most common procedure employs manual alignment with the aid of an x-ray-transmissive angle-gear system. The accuracy of this method depends on the skills of the operator. Also, it usually involves extensive exposure to radiation.

Elimination of the use of an x-ray machine is the object of the alignment devices described in German patent applications DE 4,306,724 and DE 4,414,177. However, the accuracy of these alignment devices is a function of the extent to which the intramedullary nail inserted in the bone has retained its original pre-insertion shape. These alignment devices cannot compensate for an implantation-induced bending of the nail nor any twisting between the top end and the base of the intramedullary nail. An investigation of implantation-induced deformation of solid intramedullary nails found that this is not an absolute prerequisite for accurate positioning; the twisting of solid nails is minimal and in practical application quite negligible whereas, on the other hand, there is considerable bending. It is this bending of the intramedullary nails that affects the accuracy of the aforementioned positioning devices. The results of this investigation were published in the September, 1996 issue of the journal, "Der Unfallchirurg" (The Accident Surgeon), under the title "ANALYSIS OF IMPLANTATION-INDUCED NAIL DEFORMATION AND X-RAY-MORPHOMETRIC STUDIES AS THE BASIS FOR A POSITIONAL ALIGNMENT DEVICE FOR DISTAL LOCKING WITHOUT AN X-RAY IMAGE INTENSIFIER".

An alignment device is also disclosed in Swiss patent CH 668,692. This device was designed for the purpose of permitting the axis of the hole(s) of the alignment device that is to be lined up with a hole in the distal base of the nail to be aligned with the axis of an existing hole in the distal base of a nail whenever the nail is bent or twisted between its proximal end and the holes in its distal base. This alignment device, however, requires the use of an x-ray machine. While it reduces the amount of the radiation needed, it cannot altogether do without it.

U.S. Pat. Nos. 5,281,224 and 5,433,720 describe positional alignment devices which seek to eliminate the need for an x-ray machine while at the same time tolerating some deformation of the nail upon insertion. These alignment devices are based on the concept of readjusting the alignment of the axes of the holes of the drill guide with the axes of the locking holes in the distal base of the nail using a metal detector. This metal detector uses electronic circuitry and generates a magnetic field. These inventions were sponsored by a company named ORTHOFIX S. R. L., but so far none of these alignment devices have been seen on the market.

Finally, ORTHOFIX S. R. L. has commercially introduced an alignment device in which, by means of a mandrel-shaped spacing sensor, so-called "direct contact" is possible with the anterior, forward edge of the distal base of the intramedullary nail. This alignment device is described in PCT application WO96/03085. Supposedly, this alignment device can be operated entirely without the aid of an x-ray machine, and it tolerates bends in the nail in the anteroposterior plane. In the mediolateral plane, however, the tolerable amount of nail bending is reduced to the contact surface of the positional stabilizing mandrel, which is relatively small. Furthermore, this alignment device is designed in a way that distal locking screws can be inserted only in a mediolateral orientation. Yet locking an intramedullary nail in only one single plane leaves it incomplete. For improved resistance to tilting, however, the intramedullary nails should preferably be secured along more than one single radial plane. Thus, the ORTHOFIX alignment device is deficient in this regard.

SUMMARY OF THE INVENTION

The primary invention relates to a positional alignment device for locking the base part of intramedullary nails, and which permits, without the use of x-rays, the accurate positioning of locking screws in more than one radial plane relative to the intramedullary nail. This device is useful even if on implantation the intramedullary nail is subjected to considerable bending as is commonly the case.

The present alignment device comprises an alignment device for positioning and inserting osteosynthetic fasteners in the base of an intramedullary nail implanted in a bone. This device comprises an alignment bracket detachably connectable to an intramedullary nail; a coupling unit connected to the alignment bracket; a longitudinal alignment bar having a first section which is movable within the coupling unit and a second section which includes at least one guide hole; and a first spacing-sensor assembly attachable to the second section of the alignment bar and provided with a spacing sensor having a contact surface for placement against the intramedullary nail. The first section of the alignment bar is adjustable and lockable in positionally continuous fashion within the coupling unit along the longitudinal axis of the alignment bar and is pivot-mounted to permit rotational movement relative to the alignment bracket. Also, the first spacing-sensor assembly permits the contact surface of the spacing sensor to shift transversely relative to the alignment bar to further enhance alignment.

Preferably, the spacing sensor has an L, T or edge shape. When an L or T shape is used, the shorter leg of the L or T has a length of between 2 and 40 mm. The device may include means for providing optical or audible feedback to indicate contact between the spacing sensor and the nail. In this embodiment, the contact surface of the spacing sensor may be provided with a structured profile to assist in providing the feedback. Typically, the contactor makes contact with a locking hole in the nail to do this. Also, the contactor is provided with a single- or multi-slot tip.

The first spacing-sensor assembly preferably includes a slide which is movable along an axis extending perpendicular to the alignment bar. The slide may include at least one guide channel serving to permit positioning and accommodation of the spacing sensor. The coupling unit is advantageously configured and dimensioned to allow angling of the alignment bar with relation to the alignment bracket. This can be done by angling the alignment bar about a rotary pin which extends perpendicular to the alignment bar and the spacing sensor.

If desired, a second spacing-sensor assembly can be provided. This assembly includes an alignment bridge which at one end supports a contactor that is directed at a locking hole in the nail guide holes. Also, the alignment bridge can include guide holes for receiving osteosynthetic fasteners.

Furthermore, the contactor may be provided with spacing-sensor surfaces which in the expanded state of the contactor prevent shifting of the contactor in the locking hole of the nail. The contactor may also include two interlocked, mutually telescopable spacing sensors, one of which makes contact on one side of the locking hole of the nail while the other makes contact on the other side of the locking hole of the nail.

Typically, the feedback providing means includes electric current which provides an optical or audible feedback when the contactor contacts the nail, and the alignment bracket is attachable to the nail by a screw. If desired, the alignment bar can be made to be rotatable around a pivot pin which extends perpendicular to the alignment bar and intersects an axis which extends from the screw.

BRIEF DESCRIPTION OF THE DRAWINGS

The following drawing figures illustrate the features of this invention and its a various enhancements in more detail with the aid of a partly schematic illustration of a preferred design use for on a right tibia, wherein.

DETAILED DESCRIPTION OF THE PREFERRED EMBODIMENTS

Figure 1:
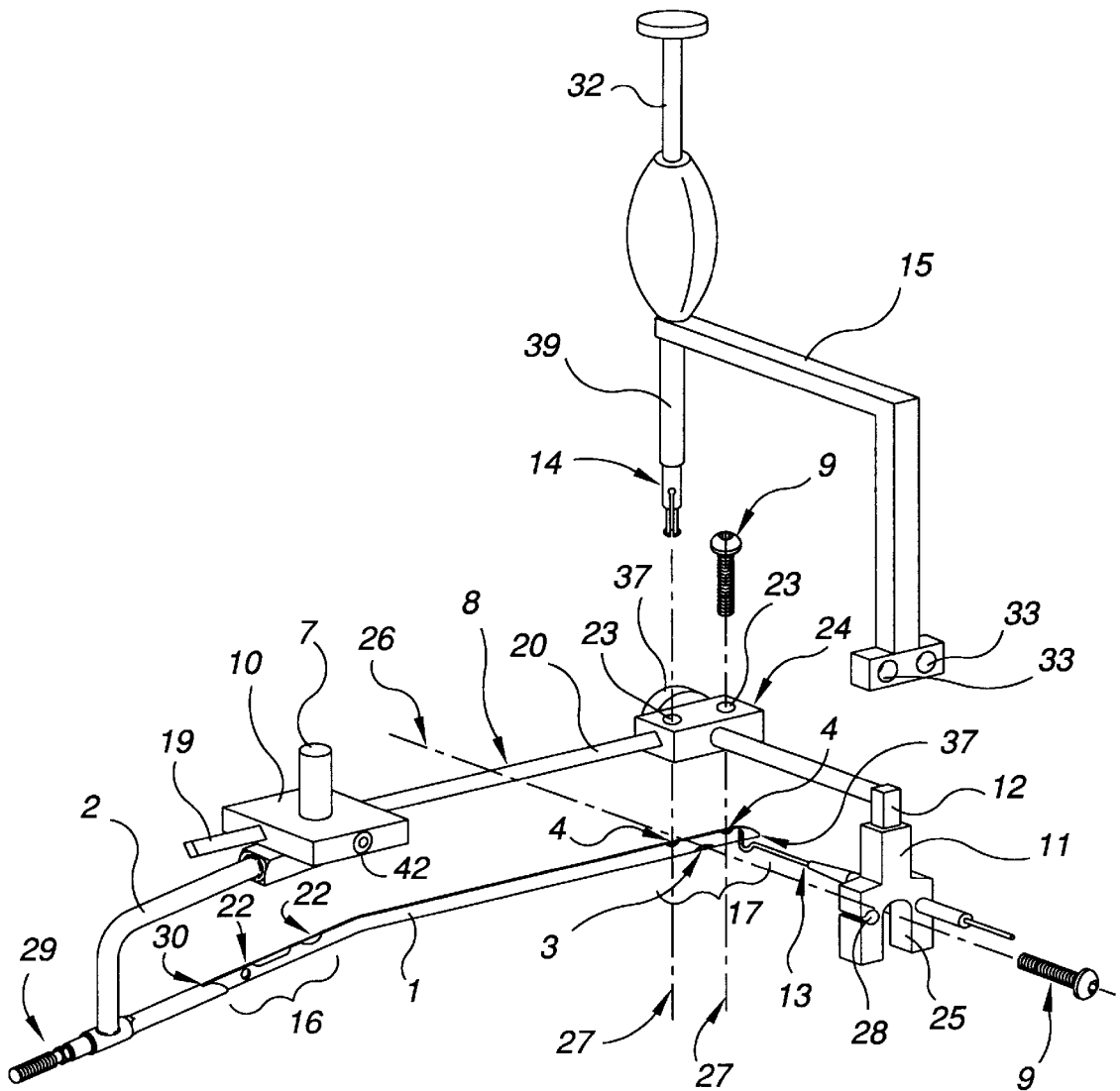
FIG. 1 is a perspective view of an alignment device according to the invention, coupled to a tibial intramedullary nail, with a first spacing sensor assembly and a second spacing sensor assembly.

The alignment device illustrated in FIG. 1 includes a longitudinal alignment bar 8 with a first section 19 and a second section 20. The first section 19 is designed as a prismatic guide and can be detachably mounted, by means of a rotationally adjustable coupling unit 10, above a standard U-shaped intramedullary-nail alignment bracket 2 at the top end 30 of the intramedullary nail. The alignment bar 8 can be longitudinally moved in the coupling unit 10 so as to permit continuously adjustable adaptation to a given, selected length of intramedullary nail.

The coupling unit 10 incorporates a pin 7 serving as a pivoting shaft which fits into the guide holes of the U-shaped alignment bracket 2. The alignment bracket 2 can be mounted at the top end 30 of the intramedullary nail 1 in conventional fashion using a screw-type fastener 29.

A drill jig 24 is mounted on the second section 20 of the alignment bar 8 and is provided with two through-holes, extending perpendicular to the alignment bar 8 and serving as mediolateral guide holes 23 for positioning and inserting mediolateral osteosynthetic fasteners 9 in the form of locking screws. The drill jig 24 is detachably connected to a first spacing sensor assembly 11, 12, 13. The latter consists of a bow-shaped spacing-sensor support 12 which on its far end from the drill jig 24 is equipped with a movable slide 11. This slide 11 is provided with an anteroposterior guide slot 25. The slide 11 also has two guide channels 28 which serve to position and accept the anterior spacing sensor 13. In FIG. 1, the distal guide channel 28 is used for that purpose, but, entirely at the option of the operator, the proximal channel 28 can perform the same function. Details of the anterior spacing sensor 13 are covered in the explanatory descriptions of FIGS. 2 and 3.

The coupling unit 10 on the first section 19 of the alignment bar 8 is so designed that it permits an angling of the alignment bar 8 relative to the attached intramedullary nail 1. Such angular change takes place around a pin 7 which extends essentially parallel to the central axis 27 of the mediolateral locking hole 4 and is preferably implemented as a pivoting joint.

The second spacing sensor assembly 14, 15 includes an alignment bridge 15 and a contact sensor. The alignment bridge 15 is provided on one side with two anteroposterior guide holes 33 used for the positioning and insertion of a fastener 9 in the anteroposterior locking hole 3 of the base 17 of the intramedullary nail 1. In the embodiment shown, involving the right tibia, the distal guide hole 33 is used. In an identical application of the alignment device on the left tibia, the guide hole 33 which is proximal in the illustration, would be positioned and used as the guide hole. The alignment bridge 15 is further provided with a contactor 14 which is aimed at a mediolateral locking hole 4 in the base 17 of the intramedullary nail 1. The contactor 14 can make contact with the locking hole 4, making it possible to verify such contact without visual or radiographic control. This can be accomplished through several different design variations which are explained below in the description of FIG. 4.

Figure 2:
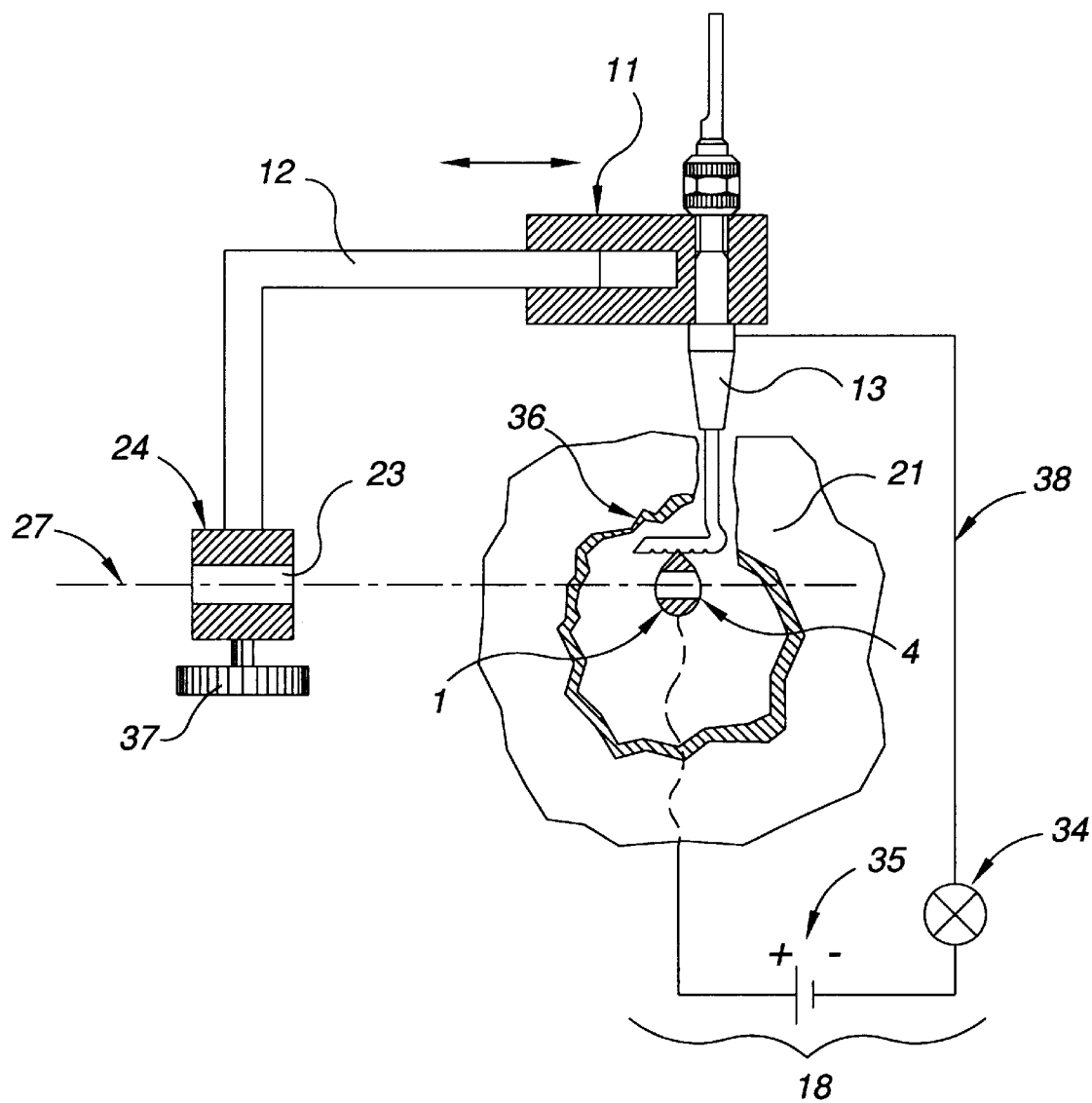
FIG. 2 shows the first spacing sensor assembly of the disclosed alignment device in intraoperative use.

FIG. 2 shows a cross section through a tibia 21. The slide 11, which can be moved in perpendicular direction relative to the alignment bar 8, and the contact surface of the anterior spacing sensor 13, which has an L-, T- or edge-shaped configuration, permit anterior contact with the nail even if that has shifted by several millimeters. The contact between the anterior spacing sensor 13 and the intramedullary nail 1 can be monitored without the use of an x-ray machine in the following manner:

1) by a metallic scraping sound of the denticulation of the contact surface of the spacing sensor 13 on the surface of the intramedullary nail 1; or 2) by optical or audible feedback or contact information resulting from a contact indicator 18, preferably one using an electric current.

The electrical contact indicator 18 of option 2 includes a power supply such as a battery, a signal transmitter 34 and an electrical wire 38 which connects the anterior spacing sensor 13 with the intramedullary nail 1. When contact between the spacing sensor 13 and the intramedullary nail 1 closes the circuit, the signal transmitter 34 provides the operator with contact information as feedback. The moment that the anterior spacing sensor 13 contacts the intramedullary nail 1, the mediolateral guide holes 23 of the drill jig 24 are aligned with the mediolateral locking holes 4 of the intramedullary nail 1.

Figure 3A:
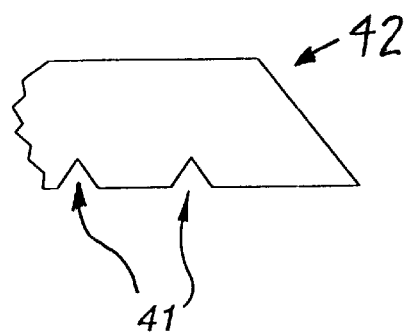
FIG. 3 shows one possible design variation of the spacing sensor of the first spacing sensor assembly, with FIG. 3A illustrating a detail of the hook portion of the sensor, and FIG. 3B and 3C depicting front and side views, respectively, of an edge shape for that portion of the sensor.
Figures 3B, 3C:
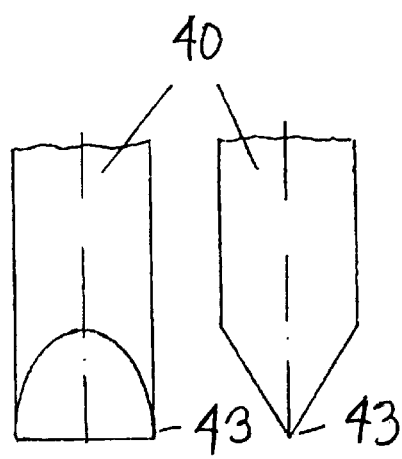
Figure 3:
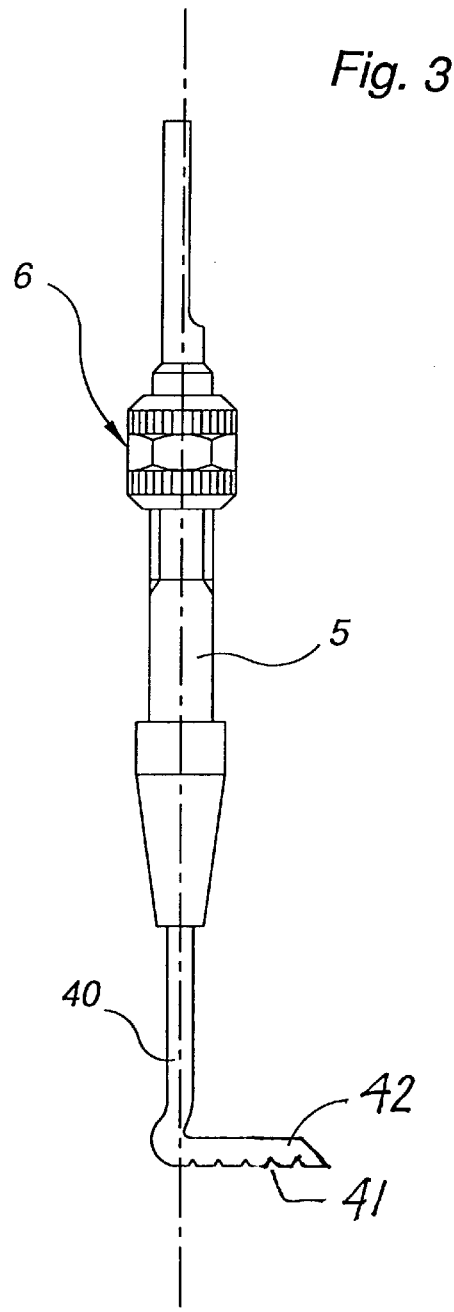

FIG. 3 shows a preferred design variation of the anterior spacing sensor 13. The L-shaped hook 40, by virtue of the contact surface on the underside of the short leg of the L touching the intramedullary nail 1, tolerates an implantation-induced bending of the intramedullary nail 1 within the length of the short leg of the L. The L-shape of the spacing sensor 13 also provides a certain amount of play for selecting the position of the contactor opening in the bone, created by the movement of the slide 11 on the spacing-sensor support 12. The notches 41 on the underside of the short leg 42 of the L of the hook 40 can produce metallic sounds on the surface of the intramedullary nail 1. These notches 41 are illustrated in FIG. 3A. A variation of the hook 40 is shown in FIGS. 3B and 3C, where an edge shape 43 is shown. Although shown as terminating in a point, edge shape 43 can also terminate in a flat land similar to that of a screwdriver head. The point is preferred for producing metallic sounds when contacting the surface of the nail 1.

These audible sounds provide the operator with feedback to the effect that the spacing sensor 13 has made contact with the intramedullary nail 1. The interchangeability of the spacing sensor 13 and the variable length of the L-, T- or edge-shaped hook 40 in the longitudinal direction of the spacing sensor 13 permit pre-operative calibration of the length between the L-, T- or edge-shaped hook 40 and the slide 11 to the selected diameter of the intramedullary nail. The fastening nut 6 permits sturdy connection of the spacing sensor 13 with the spacing-sensor support 12, including the slide 11, coupled to the alignment bar 8. This connection is made by inserting the shaft 5 of the spacing sensor 13 in the guide channel 28 and tightening the fastening nut 6.

Figure 4:
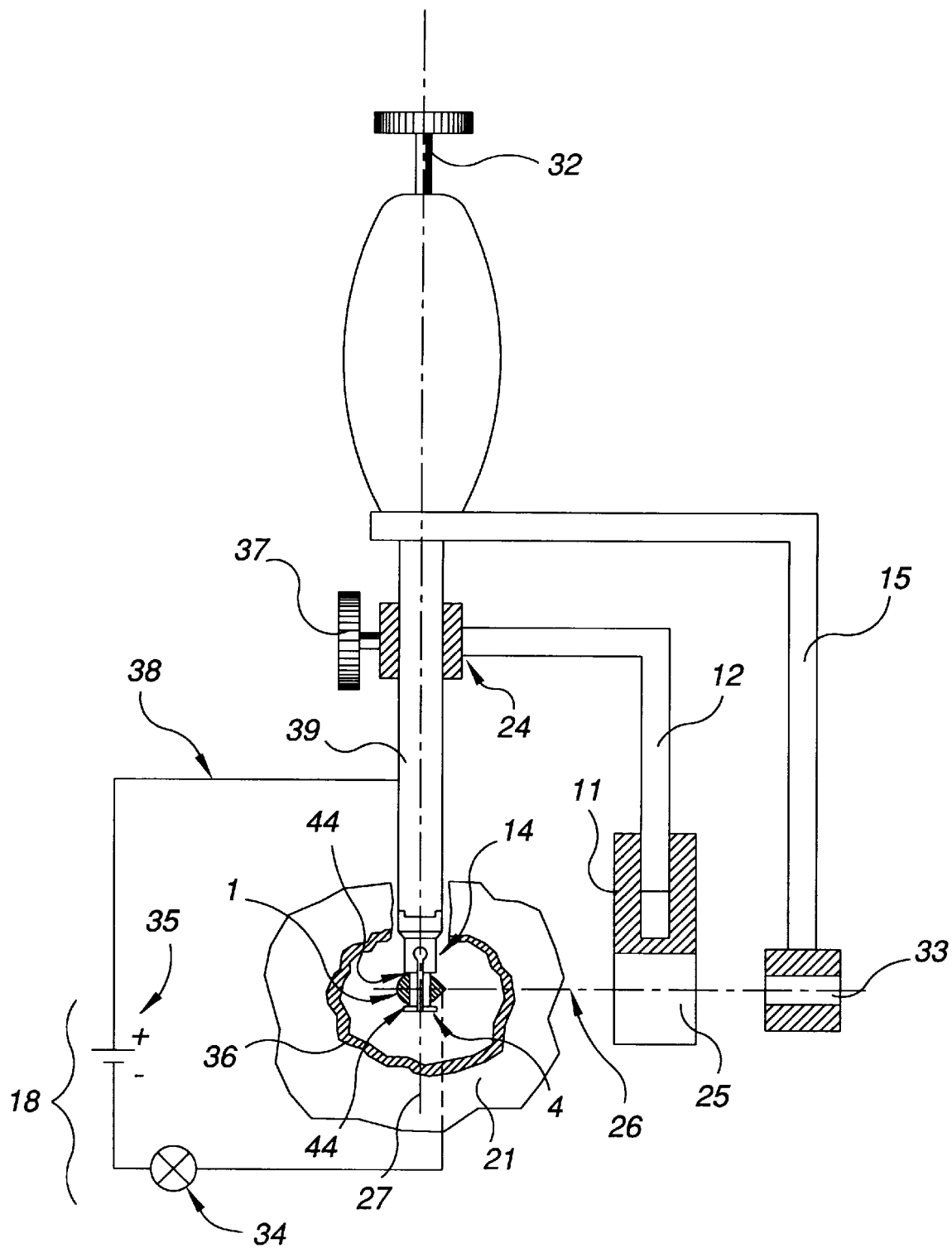
FIG. 4 is a view of the second spacing sensor assembly of the disclosed alignment device in intraoperative use.

FIG. 4 shows a cross section through the tibia 21, where the anteroposterior alignment bridge 15 is connected to one of the two mediolateral locking holes 4 of the intramedullary nail 1 by means of a contactor 14 that can be expanded using an expanding mandrel 32. This connection can be implemented in several different ways:

1) the contactor 14 can be provided with an expandable, slotted end which can be inserted in the locking hole 4 of the intramedullary nail 1. That properly secures the spacing sensor surfaces 44 through contact with the medial side of the locking hole 4 and, respectively, with the lateral side of the locking hole 4. This approach is illustrated in FIG. 4;

2) the contactor 14 can instead be secured by tightening and interlocking two spacing sensors, fitted into one another, one making contact on the medial side of the locking hole 4 and the other making contact with the lateral side of the locking hole 4;

3) a contact surface 44 can make contact with only one side of the locking hole 4 so that contact information in the form of audible feedback is provided by the sound of impact; or 4) a contact surface 44 can make contact with only one side of the locking hole 4 so that contact information in the form of optical or audible feedback can be provided by means of a contact indicator 18 which operates with an electric current. The electrical contact indicator 18 essentially consists of a power supply 35 (i.e., a battery), a signal transmitter 34 and an electric wire 38 which connects the contactor 14 to the intramedullary nail 1. When contact between the contactor 14 and the intramedullary nail 1 closes the circuit, the signal transmitter 34 provides the operator with the contact information or feedback.

As soon as there is contact between the contactor 14 and the intramedullary nail 1, the anteroposterior guide hole 33 of the alignment bridge 15 can be moved over the guide slot 25 of the spacing-sensor support 12 so that one of the anteroposterior guide holes 33 lines up with the guide slot 25. In this position the guide hole 33 will also line up with the anteroposterior locking hole 4 of the intramedullary nail 1. Only one of the guide holes 33 can be lined up with the guide slot 25; the other guide hole 33 is used for an identical application of the alignment device on a contralateral tibia.

The following will briefly explain the mode of operation of the locking of the base of an intramedullary nail employing the disclosed alignment device, using the example of a tibial intramedullary nail. The procedure consists essentially of three positioning steps:

A) Adjustment of the alignment bar (8) in the craniocaudal plane to the position of the locking holes 3, 4

A conventional, U-shaped intramedullary-nail alignment bracket 2, for instance of the type described in Swiss patent CH 668,692, is mounted on the intramedullary nail 1 which has not as yet been implanted, the said bracket 2 permitting the insertion of proximal locking screws 9 in the appropriate locking holes 22 of the intramedullary nail 1. Following that, the alignment bar 8 for the positioning and insertion of the fasteners 9 is coupled to the distal mediolateral locking holes 4 at the free end of the proximal alignment bracket 2. This is done by inserting a pivot-mount pin 7 into the guide hole of the proximal alignment bracket 2. The alignment bar 8 is then adjusted to the length of the intramedullary nail 1 used. This is done by pushing the alignment bar 8 in the coupling unit, with the set screw 42 loosened, until the guide holes 23 line up with the locking holes 4.

Thereupon the intramedullary nail 1 is inserted in the tibia, in the process of which it usually bends, making an adjustment of the alignment device in the anteroposterior and mediolateral plane necessary.

B) Adjustment of the alignment bar 8 in the anteroposterior lane to the position of the locking holes 4

The anterior edge of the base 17 of the intramedullary nail 1 is used as a reference point for the position of the mediolateral locking holes 4. The alignment bar 8 is adjusted in the anteroposterior plane by drilling a small contact opening in the bone cortex anterior to the base 17 of the implanted intramedullary nail 1. In the craniocaudal plane, the position of the contact opening is precisely defined by way of a spacing-sensor support 12 which is attached to the drill jig 24. In the mediolateral plane, the contact opening is only roughly determined; the slide 11 at the free end of the spacing-sensor support 12 allows for a certain mediolateral shifting of the contact opening in adaptation to the patient's anatomy. A special L-shaped spacing sensor 13 is pushed through this contact opening and placed onto the anterior edge of the base 17 of the intramedullary nail 1. The L-shaped spacing sensor 13 permits contact with the anterior edge of the intramedullary nail 1 from a non-centric position. After the spacing sensor 13 has been inserted, it is connected with an assembly which includes the slide 11, spacing-sensor support 12, alignment bar 8, coupling unit 10, proximal alignment bracket 2, and intramedullary nail 1. This brings the guide holes 23 into alignment with the mediolateral locking holes 4 and the bores can now be correctly positioned.

C) Adjustment of the alignment bridge 15 in the mediolateral plane to the position of the locking hole 3

For defining the placement of the bores on the anteroposterior locking hole 3, an unoccupied mediolateral locking hole 4 of the intramedullary nail 1 is used as a reference point. The alignment bridge 15, with an expandable contactor 14 coupled to it, is inserted in an unoccupied, predrilled mediolateral locking hole 4 by way of one of the guide holes 23 of the drill jig 24 attached to the alignment bar 8. Once the slotted tip of the contactor 14 has been inserted all the way in the locking hole 4 of the intramedullary nail 1, the tip can be expanded by means of an expandable mandrel 32 which latter in this case can be pushed all the way in. This defines the position of the guide holes 33 in the mediolateral plane. To define the guide holes 33 in the craniocaudal plane they must be lined up with the guide slot 25 of the slide 11 by moving the alignment bridge 15. Inserting a suitable drill-jig bush through one of the guide holes 33 of the alignment bridge 15 and the guide slot 25 causes the said guide hole 33 to line up with the anteroposterior locking hole 3 and the bore can now be placed. All locking holes 3, 4 of the intramedullary nail 1 can now accept fasteners 9 and the intramedullary nail 1 is thus radially locked in 2 different planes.

What is claimed is:

1. An alignment device for positioning and inserting osteosynthetic fasteners in an intramedullary nail implanted in a bone, said alignment device comprising:

an alignment bracket detachably connectable to an intramedullary nail;

a coupling unit connected to the alignment bracket;

a longitudinal alignment bar having a first section which is longitudinally and rotationally movable within the coupling unit and a second section which includes at least one guide hole; and a first spacing-sensor assembly attachable to the second section of the alignment bar and provided with a spacing sensor having a contact surface for placement against the intramedullary nail;

wherein:

the first section of the alignment bar is adjustable and lockable within the coupling unit for movement along the longitudinal axis of the alignment bar and is pivot-mounted within the coupling unit to permit rotational movement relative to the alignment bracket; and the first spacing-sensor assembly permits the contact surface of the spacing sensor to shift transversely relative to the alignment bar and transverse to the spacing sensor longitudinal axis.

2. An alignment device as in claim 1, wherein the spacing sensor has an L, T or edge shape.

3. An alignment device as in claim 2, wherein the spacing sensor has an L or T shape with one leg of the L or T having a length of between 2 and 40 mm.

4. An alignment device as in claim 1, wherein the contact surface of the spacing sensor is provided with a structured profile.

5. An alignment device as in claim 1, further comprising an indicator arranged to provide optical or audible feedback to indicate contact between the spacing sensor and the nail.

6. An alignment device as in the claim 1, wherein the first spacing-sensor assembly includes a slide which is movable along an axis extending perpendicular to the alignment bar.

7. An alignment device as in claim 6, wherein the slide includes at least one guide channel serving to permit positioning and accommodation of the spacing sensor.

8. An alignment device as in claim 1, wherein the coupling unit is configured and dimensioned to allow angling of the alignment bar with relation to the alignment bracket.

9. An alignment device as in claim 8, wherein the alignment bar is angled about a rotary pin which extends perpendicular to the alignment bar and the spacing sensor.

10. An alignment device as in claim 1, which further comprises a second spacing-sensor assembly which includes an alignment bridge which at one end supports a contactor that is directed at a locking hole in the nail guide holes.

11. An alignment device as in claim 10, wherein the alignment bridge includes guide holes for receiving osteosynthetic fasteners.

12. An alignment device as in claim 10, wherein the contactor makes contact with a locking hole in the nail.

13. An alignment device as in claim 12, wherein the contactor is provided with a single- or multi-slot tip.

14. An alignment device as in claim 12, wherein the contactor is provided with spacing-sensor surfaces which in the expanded state of the contactor prevent shifting of the contactor in the locking hole of the nail.

15. An alignment device as in claims 12, wherein the contactor includes two interlocked, mutually telescopable spacing sensors, one of which makes contact on one side of the locking hole of the nail while the other makes contact on the other side of the locking hole of the nail.

16. An alignment device as in claim 12, further comprising an indicator arranged to provide optical or audible feedback when the contactor contacts the nail.

17. An alignment device as in claim 16, wherein the alignment bar is rotatable around a pivot pin which extends perpendicular to the alignment bar and intersects an axis which extends from the screw.

18. An alignment device as in claim 1, wherein the first section of the alignment bar is adjustable and lockable in positionally continuous fashion.

19. An alignment device as in claim 1, wherein the alignment bracket is attachable to the nail by a screw.

* * * * *

UNITED STATES PATENT AND TRADEMARK OFFICE
CERTIFICATE OF CORRECTION

PATENT NO. : 6,039,742 Page 1 of 1
DATED : March 21, 2000
INVENTOR(S) : Christian Krettek et al.

It is certified that error appears in the above-identified patent and that said Letters Patent is hereby corrected as shown below:

<u>Title page,</u>
Item [30], Foreign Application Priority Data, add the following reference:
 -- [30]    Foreign Applicaion Priority Data
    May 4, 1996   [DE]   Germany ………….. 296 08 071.3 --.

<u>Column 8,</u>
Line 35, "claim 17" should be renumbered as claim -- 18 -- and change the dependency from "claim 16" to -- claim 17 --.
Line 35, should read -- 17.    An alignment device as in claim 1, wherein the alignment bracket is attachable to the nail by a screw. --
Line 39, "claim 18" should be renumbered as claim -- 19 --.
Line 39, should read -- 18.    An alignment device as in claim 17, wherein the alignment bar is rotatable around a pivot pin which extends perpendicular to the alignment bar and intersects an axis which extends from the screw. --
Line 42, should read -- 19.   An alignment device as in claim 1, wherein the first section of the alignment bar is adjustable and lockable in positionally continuous fashion. --
Line 43, "claim 19" should be renumbered as claim -- 17 --.

Signed and Sealed this

Fourteenth Day of December, 2004

JON W. DUDAS
*Director of the United States Patent and Trademark Office*